US006047588A

United States Patent [19]

Danilychev

[11] Patent Number: 6,047,588

[45] Date of Patent: Apr. 11, 2000

[54] AIR CARGO CONTAINER

[75] Inventor: Alexander V. Danilychev, Irvine, Calif.

[73] Assignee: McDonnell Douglas Corporation, Hazelwood, Mo.

[21] Appl. No.: 08/985,330

[22] Filed: Dec. 4, 1997

[51] Int. Cl.[7] .............................. G01N 7/00; G01M 3/02; B65D 81/20; B65D 88/00

[52] U.S. Cl. ............................ 73/23.2; 73/37; 206/524.8; 220/1.5

[58] Field of Search ................................ 73/23.36, 23.2, 73/37; 206/524.8; 220/1.5, 1.6; 200/83 C

[56] References Cited

U.S. PATENT DOCUMENTS

| | | | |
|---|---|---|---|
| 2,472,623 | 6/1949 | Schulze | 410/77 |
| 3,000,418 | 9/1961 | Bitting | 180/53.8 |
| 4,122,761 | 10/1978 | Westin et al. | 98/33 R |
| 4,243,349 | 1/1981 | Hickey et al. | 410/77 |
| 4,261,401 | 4/1981 | Hickey | 150/52 K |
| 4,911,317 | 3/1990 | Schloesser et al. | 220/1.5 |
| 4,964,309 | 10/1990 | Jenkins | 73/864.81 |
| 5,109,691 | 5/1992 | Corrigan et al. | 73/23.36 |
| 5,138,889 | 8/1992 | Conrad | 73/863.12 |
| 5,181,625 | 1/1993 | Podd et al. | 220/1.5 |
| 5,195,701 | 3/1993 | Willan | 244/118.1 |
| 5,217,132 | 6/1993 | Looker | 220/1.5 |
| 5,242,070 | 9/1993 | Bretschneider et al. | 220/1.5 |
| 5,275,361 | 1/1994 | Fray | 244/129.1 |
| 5,360,129 | 11/1994 | Lee | 220/1.5 |
| 5,377,856 | 1/1995 | Brierton | 220/1.5 |
| 5,398,831 | 3/1995 | Avramides et al. | 220/1.5 |
| 5,425,263 | 6/1995 | Davies et al. | 73/28.05 |
| 5,465,607 | 11/1995 | Corrigan et al. | 73/23.36 |
| 5,585,575 | 12/1996 | Corrigan et al. | 73/863.71 |
| 5,595,315 | 1/1997 | Podd et al. | 220/1.5 |

*Primary Examiner*—Hezron Williams
*Assistant Examiner*—Jay L. Politzer
*Attorney, Agent, or Firm*—Brooks & Kushman P.C.

[57] ABSTRACT

An air cargo container includes a relatively-rigid housing defining an air-tight interior space of nominal volume within which to receive cargo. The housing substantially maintains the nominal volume of the interior space upon pressurizing or evacuating the interior space relative to ambient pressure, whereby a differential interior pressure is achieved before loading the container aboard an aircraft. Where the differential interior pressure is achieved by pressurizing the interior space, air or another suitable gas is injected under pressure into the housing. Where the differential interior pressure is obtained by evacuating the housing's interior space, or where the process of pressurizing the interior space includes a prior evacuation step, the gases drawn from within the housing are preferably analyzed to detect the presence of contraband within the received cargo. Sensors on the housing confirm that an achieved interior pressure is substantially maintained over time.

16 Claims, 2 Drawing Sheets

12 10 28 12 18 22 20 18 28 14 16

10
12
12
28
18
22
20
18
28
14
16

24
22
12
26
10

20
20
ANALYZER
30
32

LOADING CARGO INTO INTERIOR SPACE OF CONTAINER
SEALING INTERIOR SPACE AT A FIRST AMBIENT PRESSURE
BRINGING THE INTERIOR SPACE TO A SECOND PRESSURE
MONITORING THE SECOND PRESSURE OVER TIME

AIR CARGO CONTAINER

TECHNICAL FIELD

The invention relates generally to cargo containers used in air transport and, more specifically, to air cargo containers capable of maintaining a differential interior pressure relative to ambient air subsequent to being loaded with cargo. The invention further relates to methods for monitoring air cargo containers for tampering, for detecting the presence of contraband within such containers prior to loading the container onto an aircraft, and for controlling the operation of pressure-sensitive devices, such as explosive detonators, which might otherwise be present within the container's received cargo.

BACKGROUND ART

Modern aircraft rely heavily on the use of cargo containers of standardized dimension to maximize both the aircraft's cargo carrying capacity and to expedite the loading and unloading of cargo contained in such containers. Specifically, air cargo is typically loaded into containers whose external dimensions closely match the cargo area defined within the fuselage of a given aircraft. The loaded containers are thereafter themselves loaded onto and secured within the aircraft's cargo area. In this manner, cargo may be quickly and safely loaded onto and secured within the aircraft, with the further benefit that the cargo is somewhat further protected by the container from in-flight hazzards, such as in-flight shifting due to air turbulence.

One prior art air cargo container is an aluminum monocoque structure which is typically cubic or roughly cubic in shape. At least one side wall of the container typically has an opening which provides access to the interior of the container. The opening is usually covered with a door which may itself include a rigid or semi-rigid panel or a flexible material such as fabric or netting. The prior art teaches use of tamper-resistant closure mechanisms on such prior art containers by which to provide increased security for the cargo stored within the container, and to further prevent unauthorized persons from tampering with the cargo after the container has been duly inspected for the presence of contraband.

Another prior art cargo container includes a frame or pallet and a cargo-encapsulating sealable bag. After the cargo is loaded within the bag atop the pallet, the bag is sealed and air is drawn from within the bag to collapse the bag about the cargo. In this manner, the bag is drawn closely around the cargo to thereby reduce the overall dimensions of the container while further serving to reduce the possibility of cargo shifting within the container during flight. The removal of air from within the bag further serves to remove moisture, thereby reducing the likelihood of deleterious condensation during flight which might otherwise result from the relatively lower temperatures encountered in the unheated cargo areas of many aircraft. As a further advantage, the air drawn from within the container may be analyzed for purposes of detecting the presence of contraband in the cargo.

Unfortunately, the tamper-resistant closure mechanisms of known air cargo containers and, indeed, the relatively-light construction of the such known containers themselves, are no match for determined thieves or terrorists who would tamper with an air cargo container before it is loaded onto an aircraft. More significantly, however, such known containers are incapable of providing an unambiguous indication to the aircraft loadmaster, flight crew or the like whether or not tampering has occurred after original inspection of the container.

DISCLOSURE OF INVENTION

It is an object of the invention to provide an air cargo container which provides an unambiguous indication whether or not tampering has occurred.

It is also an object of the invention to provide an air cargo container which facilitates bulk inspection of the cargo for contraband.

Another object of the invention is to provide an air cargo container whose interior pressure may be regulated so as to render harmless a pressure-sensitive device carried in the container.

Under the invention, an air cargo container includes a housing defining an air-tight interior space having a nominal volume within which to receive a cargo. The housing substantially maintains the nominal volume of the interior space as the interior space is sealed at a first ambient pressure and subsequently brought to a second pressure different from the first ambient pressure, whereby a pressure differential is achieved between the second pressure and the first ambient pressure.

In accordance with the invention, the second pressure to which the container's interior space is brought may be either less than the first ambient pressure or greater than the first ambient pressure. By way of example, where the second pressure is less than the first ambient pressure, the second pressure is preferably no greater than the flight pressure, i.e., the nominal minimum pressure to which the container is itself subjected during a flight. Thus, where an aircraft's cargo area is pressurized during flight to a predetermined minimum pressure, the second pressure is preferably slightly less than the predetermined minimum flight pressure.

Where the second pressure is greater than the first ambient pressure, the second pressure may be selected such that the cargo within the container's interior space will not experience a pressure less than the first ambient pressure, notwithstanding a slight drop in pressure within the container's interior space responsive to the relatively reduced flight pressure (the attendant increase in the pressure differential causing a slight increase in interior space volume and, hence, a slight drop in interior space pressure). In this manner, pressure-sensitive devices, such as explosive detonators, within the container may be rendered harmless.

The container further includes at least one sensor on the housing, wherein the sensors generate an output representative of the second pressure or of an achieved differential pressure. In one embodiment, the sensor generates a first visual indicator when a desired minimum differential pressure is achieved and is thereafter maintained, and a second visual indicator in the absence of such a desired minimum differential pressure. As such, the sensor may conveniently include a diaphragm valve which is responsive to the achieved pressure differential. In another embodiment, the sensor generates an output responsive to the second pressure achieved within the container's interior space.

The sensors serve to confirm that an achieved differential internal pressure is substantially maintained over time, for example, for the duration of a flight which follows such pressurization or evacuation. Unauthorized access to the cargo within the container will precipitate a loss of interior differential pressure which is detected by the sensors and, hence, communicated to the aircraft loadmaster, flight crew and others.

In accordance with another feature of the invention, the container further includes a pressure-relief valve operative to equalize the pressure of the container's interior space with a pressure exterior to the housing when the pressure differential exceeds a predetermined threshold.

While embodiments of this invention are illustrated and disclosed, these embodiments should not be construed to limit the claims. It is anticipated that various modifications and alternative designs may be made without departing from the scope of this invention.

BEST MODES FOR CARRYING OUT THE INVENTION

Figure 1:
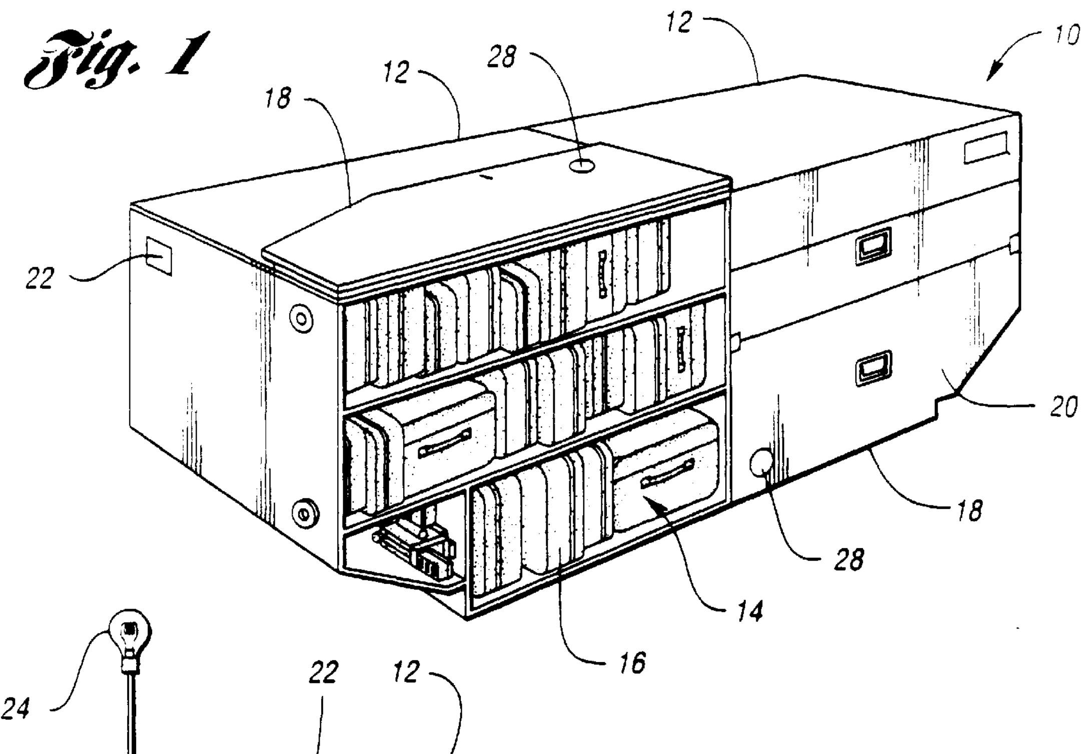
FIG. 1 is a view in perspective of a pair of exemplary half-fuselage-width baggage containers for use on a passenger aircraft in accordance with the invention.

Referring to the drawings, a pair of exemplary half-width baggage containers 10 in accordance with the invention for use aboard a DC-10 passenger aircraft are illustrated in FIG. 1. Each container 10 includes a relatively-rigid housing 12 which defines an interior space 14 of nominal volume within which to receive passenger baggage 16. A pair of hinged door panels 18 located on each side 20 of the container 10 swing upwardly to provide access to the container's interior space 14. When closed, the door panels 18 sealingly engage the housing 12 to render the interior space 14 "air-tight," i.e., capable of maintaining an achieved differential interior pressure both on the ground, when the cargo area inside the aircraft's fuselage is at ambient pressure at ground level ("ambient ground pressure"), and during flight, when the aircraft's cargo area is pressurized to a flight pressure substantially less than ambient ground pressure but substantially above ambient pressure at flight altitude.

In accordance with the invention, the relatively-rigid housing 12 of each container 10 substantially maintains the nominal volume of the container's interior space 14 upon pressurizing or evacuating the interior space 14 relative to ambient ground pressure. The housing 12 of each container 10 similarly substantially maintains the nominal volume of the container's interior space 14 during flight, i.e., when the container 10, with its pressurized or evacuated interior space 14, is subjected to a relatively reduced flight pressure.

Figure 2:
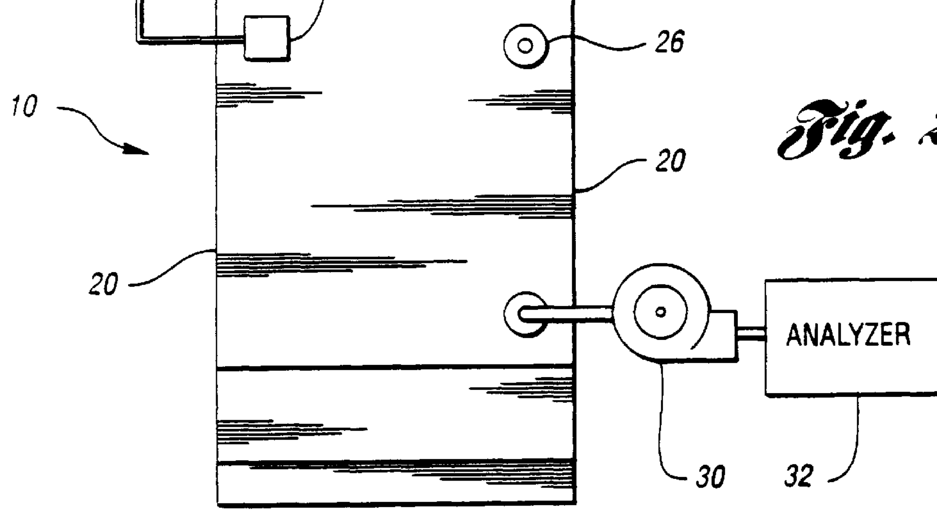
FIG. 2 is a partially schematic illustration of the baggage container of FIG. 1 connected to an exemplary apparatus for achieving an interior pressure differential and for analyzing the air drawn from within the container for the presence of contraband.

As seen in FIGS. 1 and 2, each exemplary baggage container 10 includes a first sensor 22 which generates an electrical output representative of the interior pressure differential achieved in the container's interior space 14 relative to ambient pressure. The output of the first sensor 22 preferably forms the input to a remote warning light 24 or other alarm (not shown), whereby the flight crew or others remote from the aircraft's cargo area are made aware of any breach of the container's integrity, as will occur upon tampering.

In accordance with another feature of the invention, the container 10 further includes a second sensor 26 which generates a visual indication that the differential interior pressure within the container 10 has been achieved or continues to be maintained. In a preferred embodiment, the second sensor 26 conveniently comprises a relatively low-cost, pressure-responsive diaphragm and accompanying sight glass. In this manner, the second sensor 26 provides a mechanical indication of the differential interior pressure achieved within the container 10 which may be readily checked by the aircraft's loadmaster or flight crew immediately before loading the container 10 onto the aircraft.

As seen in FIG. 1, the door panel 18 of each exemplary baggage container 10 further includes a pressure relief valve, such as a safety diaphragm 28, operative to equalize the pressure within the container's interior space 14 with the pressure exterior to the container 10 when the pressure differential exceeds a predetermined threshold. In this manner, the safety diaphragm 28 ensures that an excessive pressure differential relative to ambient pressure, as may be experienced upon sudden depressurization of the aircraft's fuselage, will rupture the safety diaphragm 28 rather than cause a catastrophic rupture of the container's housing 12. Significantly, the safety diaphragm 28 is positioned on the door panel 18 rather than on an end or bottom surface of the container 10 to thereby ensure that the fuselage is not damaged upon rupture of the safety diaphragm 28.

Figure 3:
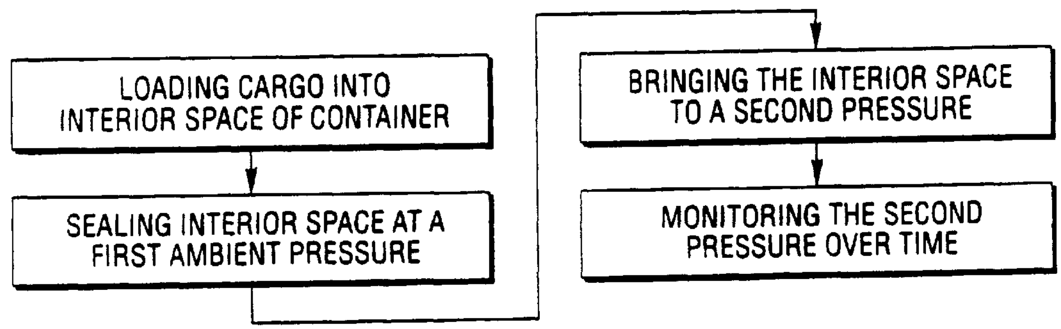
FIG. 3 is a flow chart setting forth the main steps of a method in accordance with the invention.

As illustrated in FIG. 3, in accordance with the invention, after loading the cargo 16 into the container 10 at ambient ground pressure, the interior space 14 of the container 10 is sealed by sealingly engaging the door panels 18 with the housing 12. The interior space 14 of the container 10 is then pressurized or evacuated by an air/vacuum pump 30 (as seen in FIG. 2) or in any other suitable manner to achieve a second pressure within the container 10 that is either higher or lower than the ambient ground pressure at which the container 10 was loaded. By way of example only, where the container 10 is to be loaded onto an aircraft whose cargo area in flight is pressurized to a level corresponding to about 8,000 feet of altitude, i.e., to about 11 psi, the container 10 may preferably be evacuated to achieve a second pressure of about 10 psi, i.e., slightly less than the minimum allowed cargo area pressure during flight. Preferably, the second sensor's pressure-responsive diaphragm is preferably selected such that a mechanical indication, such as a red dot appearing in the sensor's sight glass, is generated when the interior space 14 achieves the second pressure.

In this manner, a desired differential interior pressure relative to ambient ground pressure is achieved within the container 10 before the container 10 is loaded aboard the aircraft. The interior pressure within the container's interior space 14 is thereafter monitored over time to detect possible tampering with the container 10, either on the ground or during flight.

The decision whether to pressurize or evacuate a given container 10 may depend largely upon the structural properties of the housing 12, i.e., whether the housing 12 can better maintain the nominal volume of the interior space 14 when the latter is pressurized or evacuated. In any event, the invention does not contemplate the pressurization of the container's interior space 14 to so great a pressure as to significantly distort the external dimensions of the container 10, nor does the invention contemplate the evacuation of the container's interior space 14 to so little a pressure as to cause the spontaneous collapse of the container 10 about the cargo 16.

Where the differential interior pressure is achieved by pressurizing the interior space 14, air or another suitable gas is injected under pressure into the sealed housing 12. By way of example only, two suitable gases further featuring a reduced fire risk are nitrogen and argon. Such relative pressurization of the interior space 14 of the container 10, in combination with the first and second sensors 22,26, serves as a tamper indicator for the container 10, both prior to loading and during flight.

In accordance with another feature of the invention, the relative pressurization of the interior space 14 of the container 10 further serves to render harmless pressure-sensitive devices, such as explosive detonators, hidden within the cargo 16. Specifically, such devices will be rendered harmless when the interior space 14 is pressurized such that, notwithstanding a slight reduction in absolute interior pressure precipitated by a reduced flight pressure external to the housing 12, the absolute interior pressure will not drop to the device's trigger pressure. Indeed, the risk of operation of such pressure-sensitive devices may be totally minimized by pressurizing the container's interior space 14 such that the absolute interior pressure will not drop below the ambient ground pressure at which the container 10 was initially loaded.

Figure 4:
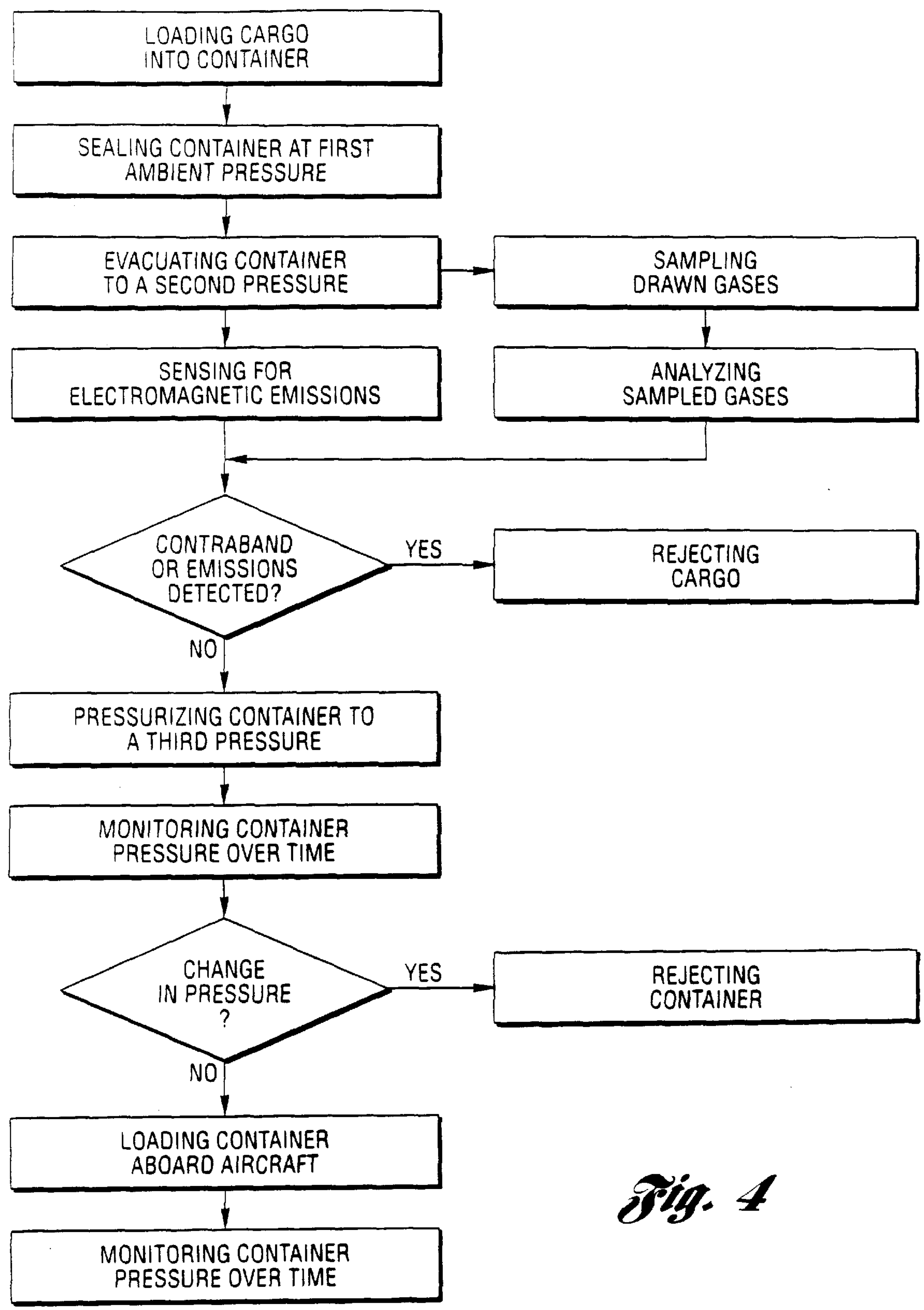
FIG. 4 is a flow chart setting forth the steps of an exemplary method in accordance with the invention.

FIG. 4 illustrates an exemplary method in accordance with the invention wherein, after the cargo 16 is loaded into the container's interior space 14 at ambient ground pressure and the container 10 is sealed, the differential interior pressure is achieved in two discrete phases: in the first phase, the container's interior space 14 is evacuated to a predetermined second pressure. The gases drawn from the container's interior space 14 during the evacuation step are sampled and analyzed in a gas chromatograph, mass spectrometer or other suitable detector 32 (as seen in FIG. 2). In this manner, the presence of drugs, explosives or other substances within the received cargo 16 are readily detected.

To the extent that depressurization of the interior space 14 of the container 10 may itself trigger a pressure-sensitive device, the invention contemplates taking such precautions as are reasonably necessary to prevent injury during the depressurization step. Moreover, since the pressure-sensitive device may include a time-delay device, in the exemplary method illustrated in FIG. 4, the evacuation step is preferably followed by sensing for electromagnetic emissions originating within the interior space 14 of the container 10.

If contraband or electromagnetic emissions are detected, the cargo 16 is immediately rejected, i.e., the subject container 10 is removed to a relatively remote location, its differential interior pressure is relieved, and its cargo 16 checked.

If, on the other hand, neither contraband nor electromagnetic emissions are detected, in the second phase by which to achieve the subject differential interior pressure, the container's interior space 14 is pressurizing to a third pressure greater than ambient ground pressure. For example, in a preferred method, argon gas is injected under pressure into the interior space 14 of the container 10 to achieve the desired third pressure.

The interior pressure thus achieved within the container's interior space 14 is thereafter monitored for a predetermined minimum time to confirm the airtight integrity of the container 10. If the interior pressure drops, the container 10 is itself rejected, i.e., any remaining pressure differential is relieved and the cargo 16 is removed from the container 10 for placement in another container 10. If the static pressure within the container 10 remains constant for the predetermined minimum time, the container 10 has passed inspection and may be loaded onto an aircraft. In accordance with another feature of the invention, the container 10 is thereafter monitored, both on the ground and in flight, to detect any tampering with the loaded container 10.

While embodiments of the invention have been illustrated and described, it is not intended that these embodiments illustrate and describe all possible forms of the invention. Rather, it is intended that the following claims cover all modifications and alternative designs, and all equivalents, that fall within the spirit and scope of this invention. For example, while the door panels 18 of the exemplary baggage container 10 sealingly engage the housing 12 to provide an air-tight interior space 14, it will be appreciated that, under the invention, the container 10 may be rendered "air-tight" in any suitable manner, as through the use of internal or external bags or other structures which may themselves be sealingly closed after the cargo 16 is placed within the housing 12.

What is claimed is:

1. A container for transporting a cargo comprising:

a housing defining an air-tight interior space having a nominal volume at a first ambient pressure within which to receive the cargo at the first ambient, wherein the housing substantially maintains the nominal volume of the interior space as the interior space is brought to a second pressure different from the first ambient pressure, whereby a first pressure differential is achieved between the second pressure and the first ambient pressure, and whereby a second differential pressure is achieved between the second pressure and a third pressure external to the container to which the container is subjected during transportation; and at least one sensor on the housing, wherein the sensor generates an output responsive to at least one of the group consisting of the second pressure, the first differential pressure, and the second differential pressure.

2. The container of claim 1, wherein the second pressure is less than the first pressure.

3. The container of claim 2, wherein the third pressure is a nominal minimum pressure to which the container is subjected during a flight of an aircraft onto which the container is loaded, and wherein the second pressure is less than the third pressure.

4. The container of claim 1, wherein the second pressure is greater than the first pressure.

5. The container of claim 1, wherein the sensor generates a first signal when at least one of the group consisting of the second pressure, the first differential pressure and the second differential pressure exceeds a first threshold value, and wherein the sensor generates a second signal when at least one of the group consisting of the second pressure, the first differential pressure, and the second differential pressure does not exceed the first threshold value.

6. The container of claim 1, wherein the sensor includes a diaphragm valve responsive to the first and second pressure differentials, and wherein the first and second signals include a visual indicator.

7. The container of claim 1, including a normally-closed pressure-relief valve connecting the interior space to an area external to the container that opens to equalize the second pressure with the third pressure when the second pressure differential exceeds a second threshold value.

8. A method for use with a cargo container, wherein the container includes an interior space having a substantially-fixed-volume loaded with a cargo, the method comprising:

sealing the interior space at a first ambient pressure;

bringing the interior space to a second pressure substantially different from the first ambient pressure, whereby a first pressure differential is achieved between the second pressure and the first ambient pressure; and monitoring at least one of the group consisting of the second pressure and the first pressure differential.

9. The method of claim 8, wherein bringing the interior space to the second pressure includes pressurizing the interior space.

10. The method of claim 8, wherein bringing the interior space to the second pressure includes evacuating the interior space, whereby gases are drawn from within the interior space.

11. The method of claim 8, including generating a first signal when at least one of the group consisting of the second pressure and the first differential pressure exceed a first threshold value, and generating a second signal when at least one of the group consisting of the second pressure and the first differential pressure does not exceed the first threshold value.

12. The method of claim 10, further including analyzing the drawn gases for the presence of contraband.

13. The method of claim 8, further including subjecting the sealed container to a third pressure external to the container, whereby a second differential pressure is achieved between the second pressure and the third pressure; and wherein monitoring includes monitoring the second pressure differential.

14. The method of claim 13, wherein the third pressure is a nominal minimum pressure to which the container is subjected during a flight of an aircraft onto which the container is loaded, and wherein the second pressure is less than the third pressure.

15. The method of claim 8, including generating a third signal when at least one of the group consisting of the second pressure, the first differential pressure, and the second differential pressure exceed a second threshold value, and generating a fourth signal when at least one of the group consisting of the second pressure, the first differential pressure, and the second differential pressure does not exceed the second threshold value.

16. The method of claim 8, including equalizing the second pressure with a third pressure external to the container when the second pressure differential exceeds a third threshold value.

* * * * *